United States Patent
Ueda et al.

(10) Patent No.: US 9,884,177 B2
(45) Date of Patent: Feb. 6, 2018

(54) CONNECTOR ASSEMBLY, MALE CONNECTOR, AND FEMALE CONNECTOR

(71) Applicant: Terumo Kabushiki Kaisha, Tokyo (JP)

(72) Inventors: Yasuhiro Ueda, Tokyo (JP); Takashi Tsukada, Tokyo (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 1116 days.

(21) Appl. No.: 14/033,728

(22) Filed: Sep. 23, 2013

(65) Prior Publication Data
US 2014/0021714 A1    Jan. 23, 2014

Related U.S. Application Data

(63) Continuation of application No. PCT/JP2012/057345, filed on Mar. 22, 2012.

(30) Foreign Application Priority Data

Mar. 24, 2011 (JP) ................ 2011-066069

(51) Int. Cl.
*A61M 39/10* (2006.01)
*F16L 37/138* (2006.01)
(Continued)

(52) U.S. Cl.
CPC ........ *A61M 39/1011* (2013.01); *F16L 37/101* (2013.01); *F16L 37/138* (2013.01);
(Continued)

(58) Field of Classification Search
CPC ...... A61M 39/1011; A61M 2039/1088; A61M 2039/1016; A61M 2039/1027;
(Continued)

(56) References Cited

U.S. PATENT DOCUMENTS 2,877,027 A * 3/1959 Bagnell ................ F16L 33/01
                                                    285/113
4,895,570 A    1/1990 Larkin
(Continued)

FOREIGN PATENT DOCUMENTS

EP    1 902 747 A2    3/2008
GB    2 451 891 A     2/2009
(Continued)

OTHER PUBLICATIONS

Extended European Search Report dated Jul. 7, 2014 issued in 12761074.9.
(Continued)

*Primary Examiner* — James M Hewitt, II
(74) *Attorney, Agent, or Firm* — Foley & Lardner LLP (57) ABSTRACT

A connecter assembly includes a male connecter and a female connecter that are connected to each other. The male connecter includes a connecter main body; an engagement member including a support portion which fixedly supports the connecter main body, a plurality of claw portions, and a plurality of slit portions; and a lock member disposed outside the engagement member and including a plurality of ribs that are slidably insertable into each of the plurality of slit portions of the engagement member. The female connecter includes a main body portion including: a plurality of flange portions protruding in a radially outward direction so as to be engagable with each of the plurality of claw portions of the engagement member, and a plurality of non-flange portions that are disposed between the plurality of flange portions, and when compared to the flange portion, bulged in a radially outward direction.

18 Claims, 11 Drawing Sheets

(51) Int. Cl.
*F16L 37/10* (2006.01)
*F16L 23/00* (2006.01)

(52) U.S. Cl.
CPC ............ *A61M 2039/1016* (2013.01); *A61M 2039/1027* (2013.01); *A61M 2039/1088* (2013.01); *F04C 2270/0421* (2013.01); *F16L 23/003* (2013.01)

(58) Field of Classification Search
CPC ..... F16L 37/101; F16L 37/103; F16L 37/105; F16L 37/138
USPC .................................................. 285/86, 243
See application file for complete search history.

(56) References Cited

U.S. PATENT DOCUMENTS

| | | | |
|---|---|---|---|
| 6,077,259 | A | 6/2000 | Caizza et al. |
| 6,880,587 | B1* | 4/2005 | Carter ................ B60H 1/00585 141/383 |
| 7,543,858 | B1* | 6/2009 | Wang ................. F16L 37/0982 285/314 |
| 2004/0087986 | A1 | 5/2004 | Ott |
| 2005/0082828 | A1 | 4/2005 | Wicks et al. |
| 2005/0143714 | A1 | 6/2005 | Hegland et al. |
| 2006/0033331 | A1* | 2/2006 | Ziman ................. A61M 39/10 285/330 |
| 2007/0225648 | A1* | 9/2007 | Winsor ............... A61M 39/045 604/167.04 |
| 2010/0295292 | A1* | 11/2010 | Wang ..................... F16L 37/138 285/24 |
| 2011/0074148 | A1 | 3/2011 | Imai |
| 2011/0270230 | A1* | 11/2011 | Sage ..................... A61M 39/12 604/533 |

FOREIGN PATENT DOCUMENTS

| | | |
|---|---|---|
| JP | 08-243171 A | 9/1996 |
| JP | S-50-115823 U | 9/1997 |
| JP | 2000-107300 A | 4/2000 |
| JP | 2002-126094 A | 5/2002 |
| JP | 2005-536243 A | 12/2005 |
| WO | WO-2006/036192 A1 | 4/2006 |
| WO | WO-2009/010998 A1 | 1/2009 |
| WO | WO-2009/133754 A1 | 11/2009 |

OTHER PUBLICATIONS

International Search Report dated May 22, 2012 issued in Application No. PCT/JP2012/057345.

Japanese Office Action issued in Japanese Patent Applicatino No. 2013-506002 dated Nov. 17, 2015.

* cited by examiner

CONNECTOR ASSEMBLY, MALE CONNECTOR, AND FEMALE CONNECTOR

CROSS-REFERENCE TO RELATED APPLICATIONS

This application is a continuation application filed under 35 U.S.C. 111(a) claiming the benefit under 35 U.S.C. §§ 120 and 365(c) of PCT International Application No. PCT/JP2012/057345 filed on Mar. 22, 2012, which is based upon and claims the benefit of priority of Japanese Application No. 2011-066069 filed on Mar. 24, 2011, the entire contents of which are hereby incorporated by reference in their entireties.

BACKGROUND

The present disclosure relates to a connecter which is used as a medical tool.

An infusion set for injecting a drug solution into a patient has been widely used as a medical tool. In the middle of the flow path of the infusion set, a flow path for injecting other drug solutions may be further connected using a pair of connecters. When such an additionally connected flow path is no longer required, the additional flow path is separated by disconnecting the connecters.

In this case, regardless of whether or not the connecters are connected to each other, it is important that the inside of the flow path is not contaminated with bacteria and the like. For example, in Japanese Patent Publication No. JP-A-2000-107300, a technology is disclosed in which, by providing a valve in each connecter and keeping the inside of the flow path from being exposed to outside except when the connecters are connected to each other, the inside of the flow path may be inhibited from being contaminated with bacteria and the like.

However, in the connecters of the related art, including the connecter of Japanese Patent Publication No. JP-A-2000-107300, if a connection between the connecters is achieved using a certain operation (for example, 'push', 'twist', and the like), a disconnection of the connecters is also achieved using that same operation (for example, 'pull', 'twist', 'push button', and the like), and there is a problem that disconnection of connectors is likely to occur in unintended situations. For example, disconnection of connecters may occur by pulling a tube connected to the connecters, for example, by tossing and turning, and other movements of a patient.

In addition, it is also possible not to make the connecters disconnectable from each other. However, in this case, the connection operation is complicated, and this is not practically preferable.

Accordingly, embodiments of the present invention have been made in view of such problems, and aim to facilitate connection between the connecters and to reduce possibility of disconnection between the connecters in unintended situations.

SUMMARY

In one embodiment, a connecter assembly comprises a male connecter and a female connecter that are connected to each other. The male connecter includes a connecter main body; an engagement member including a support portion which fixedly supports the connecter main body, a plurality of claw portions engaging with the female connecter, and a plurality of slit portions provided between the plurality of claw portions; and a lock member disposed outside the engagement member and including a plurality of ribs that are slidably insertable into each of the plurality of slit portions of the engagement member. The female connecter includes a main body portion, the main body portion including: a plurality of flange portions protruding in a radially outward direction so as to be engagable with each of the plurality of claw portions of the engagement member of the male connecter, and a plurality of non-flange portions that are disposed between the plurality of flange portions, and when compared to the flange portion, bulged in a radially outward direction. The male connecter and the female connecter are configured such that, when the male connecter is connected to the female connecter, the connecter main body of the male connecter is connected to the female connecter, and the plurality of claw portions of the engagement member of the male connecter engage with respective ones of the plurality of flange portions of the main body portion of the female connecter, thereby fixing the male connecter to the female connecter.

In another embodiment, a male connecter is provided that is connectable to a female connecter that includes a main body portion, a plurality of flange portions protruding in a radially outward direction, and a plurality of non-flange portions that are disposed between the plurality of flange portions, and, when compared to the flange portion, bulged in the radially outward direction over the entire axial direction. The male connecter comprises a connecter main body; an engagement member including a support portion which fixedly supports the connecter main body, a plurality of claw portions engaging with the female connecter, and a plurality of slit portions provided between the plurality of claw portions; and a lock member disposed outside the engagement member and including a plurality of ribs that are slidably insertable into each of the plurality of slit portions of the engagement member. The male connecter is configured such that, when the male connecter is connected to the female connecter, the connecter main body of the male connecter is connected to the female connecter, and the plurality of claw portions of the engagement member of the male connecter engage with respective ones of the plurality of flange portions of the main body portion of the female connecter, thereby fixing the male connecter to the female connecter.

In another embodiment, a female connecter is provided that is connectable to a male connecter that includes a connecter main body; an engagement member that includes a support portion fixedly supporting the connecter main body inside, a plurality of claw portions, and a plurality of slit portions provided between the plurality of claw portions; and a lock member that is disposed outside the engagement member and has a plurality of ribs that are slidably inserted into each of the plurality of slit portions of the engagement member. The female connecter comprises a main body portion, the main body portion including: a plurality of flange portions protruding in a radially outward direction so as to be engagable with each of the plurality of claw portions of the engagement member of the male connecter, and a plurality of non-flange portions that are disposed between the plurality of flange portions, and when compared to the flange portion, bulged in a radially outward direction. The female connecter is configured such that, when the male connecter is connected to the female connecter, the connecter main body of the male connecter is connected to the female connecter, and the plurality of claw portions of the engagement member of the male connecter engage with respective ones of the plurality of flange portions of the main body portion of the female connecter, thereby fixing the male connecter to the female connecter.

DETAILED DESCRIPTION

Embodiments of the invention provide a connecter assembly including a male connecter and a female connecter connected to each other. The male connecter includes a connecter main body, an engagement member, the whole of which is in a substantially cylindrical shape, and which has a support portion fixedly supporting the connecter main body inside, a plurality of claw portions engaging with the female connecter, and a plurality of slit portions provided between the plurality of claw portions, and a lock member, the whole of which is in a substantially cylindrical shape, and which is disposed outside the engagement member, and has a plurality of ribs which are slidably inserted into each of the plurality of slit portions of the engagement member inside. The female connecter includes a main body portion, the whole of which is in a substantially cylindrical shape, and which has a plurality of flange portions protruding in a radially outward direction so as to be engaged with each of the plurality of claw portions of the engagement member of the male connecter, and a plurality of non-flange portions provided between the plurality of flange portions, and compared to the flange portion, bulged in the radially outward direction over the entire axial direction.

Each of the male connecter and the female connecter, when the male connecter is connected to the female connecter, has a connecter main body of the male connecter connected to the female connecter, and at the same time each of the plurality of claw portions of the engagement member of the male connecter engaged with each of the plurality of flange portions of the main body portion of the female connecter, thereby, the male connecter is fixed to the female connecter.

Accordingly, it is possible to perform a connection operation between connecters (male connecter and female connecter) in one operation. In the connection operation between the connecters, by pressing into each other, while connecting the connecter main body of the male connecter to the female connecter, each of the plurality of claw portions of the engagement member of the male connecter is engaged with each of the plurality of flange portions of the main body portion of the female connecter. Accordingly, it is possible to stably fix the male connecter and the female connecter.

Accordingly, it is possible to facilitate connection between the connecters and to reduce possibility of disconnection between the connecters in an unintended situation.

In addition, it is preferable that in each of the male connecter and the female connecter, when the male connecter is disconnected from the female connecter, if the lock member of the male connecter is moved in a direction away from the plurality of claw portions of the engagement member, the plurality of claw portions of the engagement member is made to open in the radially outward direction since restriction of movement with respect to the radially outward direction by the lock member is released, and then, the engagement member is rotated in the circumferential direction when the lock member is rotated in a circumferential direction, and each of the plurality of claw portions of the engagement member of the male connecter moves to each of the plurality of non-flange portions from each of the plurality of flange portions of the main body portion of the female connecter, thereby the male connecter can be disconnected from the female connecter.

Accordingly, it is possible to perform the disconnection operation between the connecters as two operations. That is, in the disconnection operation between the connecters, by a first operation of pulling away the lock member of the male connecter from the engagement member and a second operation of rotating the lock member, firstly each of the plurality of claw portions of the engagement member of the male connecter is moved to each of the plurality of non-flange portions from each of the plurality of flange portions of the main body portion of the female connecter to enable disconnection between the male connecter and the female connecter.

Therefore, it is possible to reduce possibility of disconnection between the connecters in the unintended situations and to concretely realize a configuration of enabling disconnection between the connecters.

In addition, each of the plurality of claw portions of the engagement member of the male connecter and each of the plurality of non-flange portions of the female connecter preferably have portions in a mountain shape which oppose each other when the male connecter and the female connecter are connected to each other.

Accordingly, when performing a connection operation between the male connecter and the female connecter, even without the positioning of the circumferential direction, each of the plurality of claw portions of the engagement member of the male connecter is induced to a position of the flange portion from the plurality of non-flange portions of the female connecter, so that the connection operation is facilitated.

The above-mentioned male connecter and female connecter may not be manufactured at the same time by the same person, and, for example, may be separately manufactured and used together at the time of use.

According to embodiments of the invention, it is possible to facilitate connection between the connecters and to reduce possibility of disconnection between the connecters in unintended situations.

Hereinafter, an embodiment (hereinafter, referred to as the embodiment) for carrying out the present invention will be described with reference to the drawings. In the present embodiment, vertical, clockwise, and counter-clockwise directions are applied to FIGS. 2A to 5C in the same manner as illustrated in FIG. 1.

Figure 1:
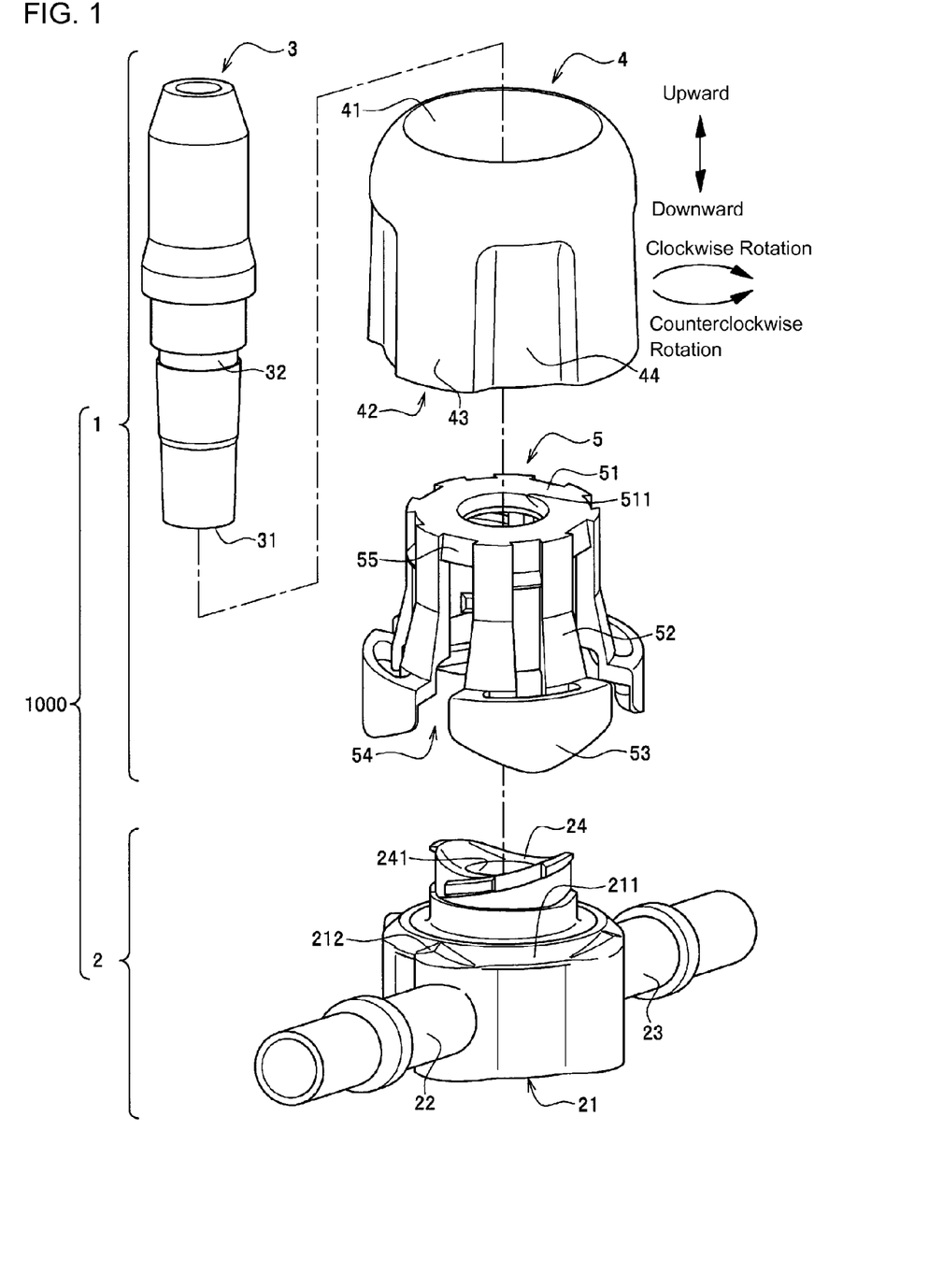
FIG. 1 is an exploded perspective view of a connecter assembly according to one embodiment.

As illustrated in FIG. 1, a connecter assembly 1000 includes a male connecter 1 and a female connecter 2.

The male connecter 1 includes a connecter main body 3, a lock member 4, and an engagement member 5. The material thereof has some extent of flexibility, durability and the like, and may be, for example, a synthetic resin such as polycarbonate, polyacetal, polypropylene, polyacrylamide, polyethylene terephthalate, or the like, but is not limited thereto.

The connecter main body 3 has a flow path inside, and includes a tip portion 31 and a supported portion 32 slightly recessed so as to be supported by a hole portion 511 of the upper surface portion 51 of an engagement member 5.

The lock member 4, the whole of which is in a substantially cylindrical shape, is a member disposed outside the engagement member 5 at the time of use. The lock member 4 includes opening portions 41 and 42, a convex portion 43 which has a plurality of ribs 431 (refer to FIG. 2B) slidably inserted into each of a plurality of slit portions 54 of the engagement member 5, and a plurality of concave portions 44 disposed between the plurality of convex portions 43.

The engagement member 5, the whole of which is in a substantially cylindrical shape, is a member engaging with the female connecter 2. The engagement member 5 includes an upper surface portion 51 having the hole portion 511 (support portion) fixedly supporting a supported portion 32 of the connecter main body 3 which is inserted, a claw support portion 52 whose one end is fixed to the upper surface portion 51, a plurality of claw portions 53 engaging with the female connecter 2, a plurality of slit portions 54 provided between the plurality of claw portions 53, and a stopper 55 positioned on the extension of the opening direction of the slit portion 54. The claw portion 53 has a claw 531 inside (refer to FIGS. 2B and 2C).

The female connecter 2 includes a main body portion 21, ports 22 and 23, a valve body support portion 24, and a valve body 241.

The main body portion 21, the whole of which is in a substantially cylindrical shape, has a plurality of flange portions 211 protruding in a radially outward direction so as to be engaged with each of claws 531 of the plurality of claw portions 53 of the engagement member 5 of the male connecter 1. In addition, between the plurality of flange portions 211, compared to the flange portion 211, a plurality of non-flange portions 212 are bulged in a radially outward direction over an entire axial length of the non-flange portions 212.

Each of the plurality of claw portions 53 of the engagement member 5 of the male connecter 1 and each of the plurality of non-flange portions 212 of the female connecter 2 have portions in a mountain shape which oppose each other when the male connecter 1 and the female connecter 2 are connected to each other. Accordingly, when performing a connection operation between the male connecter 1 and the female connecter 2, even without the positioning of the circumferential direction, each of the plurality of claw portions 53 of the engagement member 5 of the male connecter 1 are induced to a position of the flange portion 211 from the plurality of non-flange portions 212 of the main body portion 21 of the female connecter 2, thereby facilitating the connection operation.

Ports 22 and 23 are members for connecting medical tubings, and have a flow path inside.

Figure 3A:
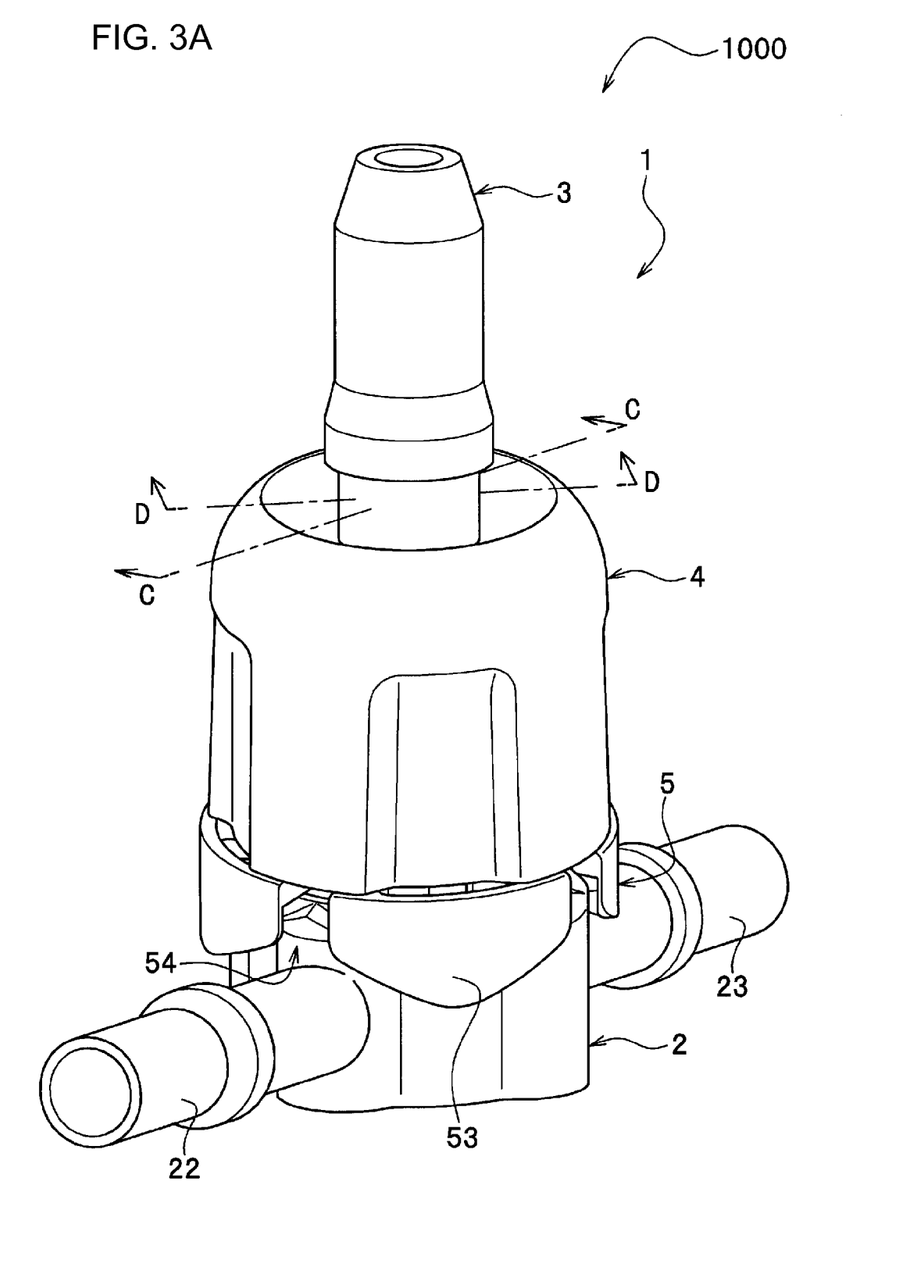
FIG. 3A is a perspective view of the connecter assembly where the male connecter and a female connecter are connected.
Figure 3B:
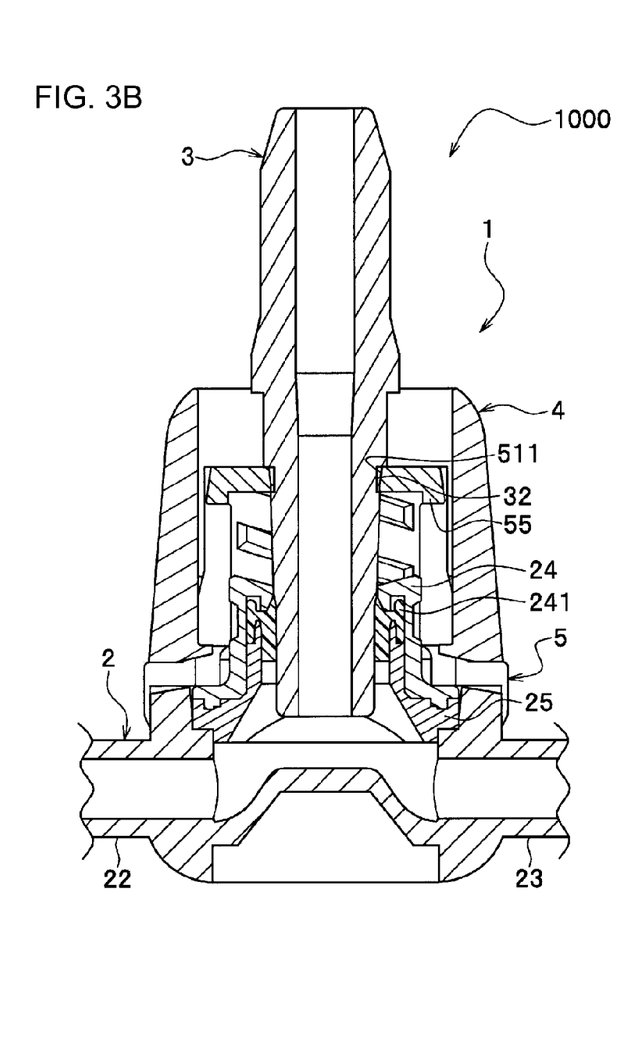
FIG. 3B is a cross-sectional diagram of the connecter assembly taken along the line C-C of FIG. 3A.
Figure 3C:
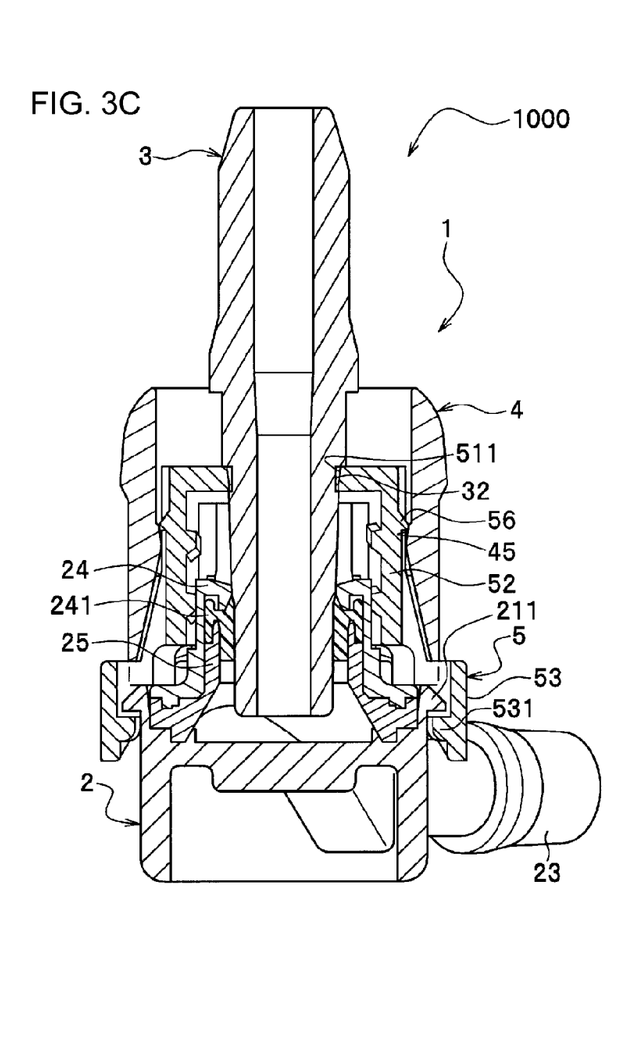
FIG. 3C is a cross-sectional diagram of the connecter assembly taken along the line D-D of FIG. 3A.

The valve body 241 is a member connected to the connecter main body 3 of the male connecter 1, and is supported by the valve body support portions 24 and 25 (refer to FIG. 3B).

Figure 2A:
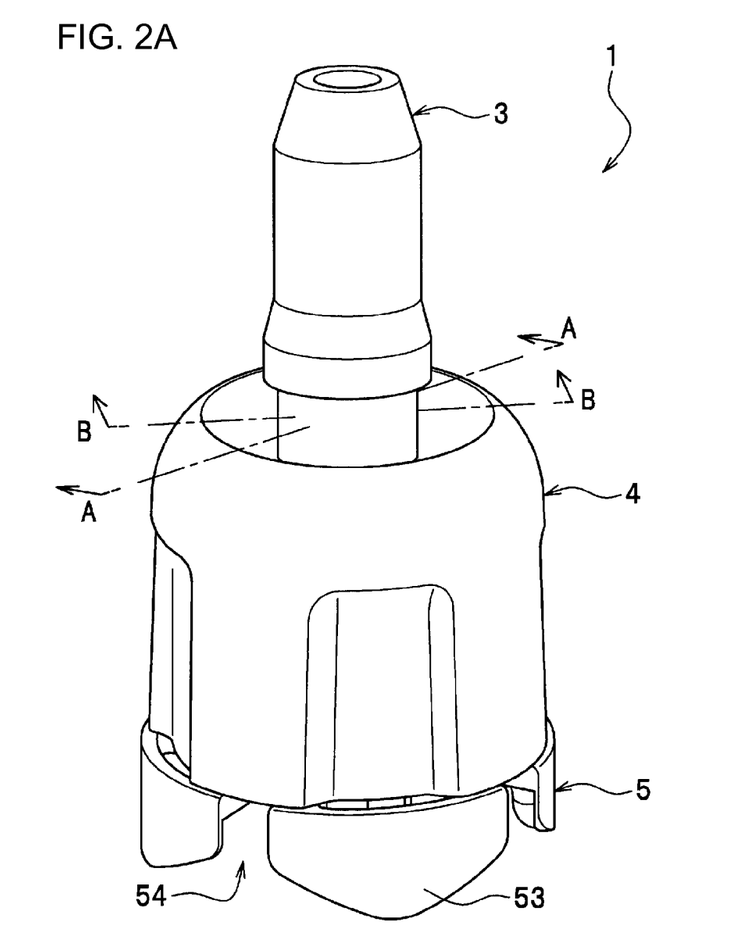
FIG. 2A is a perspective view of a male connecter according to one embodiment.

Next, referring to FIGS. 1 to 2C, an operation of connecting the connecter main body 3, the lock member 4, and the engagement member 5 in the male connecter 1 will be described.

First, by inserting the connecter main body 3 from the tip portion 31 side into the hole portion 511 of the upper surface portion 51 of the engagement member 5 from above, the supported portion 32 of the connecter main body 3 and the hole portion 511 of the upper surface portion 51 of the engagement member 5 are engaged to each other. (refer to FIGS. 2B and 2C).

Next, the connecter main body 3 and the engagement member 5 which are engaged to each other are inserted to the lock member 4 from the bottom, that is, from an opening portion 42 side. An outer peripheral surface portion of the stopper 55 is tapered (refer to FIG. 2B), so that a force needed when the ribs 431 of the lock member 4 passes through the side of the stopper 55 of the engagement member 5 is small. When the bottom of the lock member 4 and the engagement member 5 are connected to each other, the convex portion 45 and the rib 56 slightly come into contact with each other, respectively, thereby the lock member 4 and the engagement member 5 are slightly fixed (refer to FIG. 2C). Hereinafter, the male connecter 1 in a state illustrated in FIG. 2A is referred to as a connected male connecter 1.

Next, referring to FIGS. 1 to 3C, an operation of connecting the connected male connecter 1 and the female connecter 2 will be described.

The connected male connecter 1 and the female connecter 2 get close to each other in a state of relative position so that the claw portion 53 of the engagement member 5 may oppose the flange portion 211 and the non-flange portion 212 of the main body portion 21.

Then, the upper portion of the flange portion 211 is tapered, so that, using a small force, the claw 531 of the engagement member 5 passes through the side of the flange portion 211 of the main body portion 21, the claw 531 is engaged with the flange portion 211, the connected male connecter 1 is connected to the female connecter 2, thereby these are fixed to each other (refer to FIG. 3B). Here, the connecter main body 3 is connected to the valve body 241 of the female connecter 2.

Each of the plurality of claw portions 53 of the engagement member 5 of the male connecter 1 and each of the plurality of non-flange portions 212 of the female connecter 2 are in a mountain shape. Accordingly, when performing a connection operation between the male connecter 1 and the female connecter 2, even without the positioning of the circumferential direction, each of the plurality of claw portions 53 of the engagement member 5 of the male connecter 1 is induced to a position of the flange portion 211 from the plurality of non-flange portions 212 of the female connecter 2, so that it is possible to easily perform the connection operation.

Hereinafter, the connecter assembly 1000 in a state illustrated in FIG. 3A is referred to as "a connected connecter assembly 1000". In addition, a C-C cross-sectional view of the connected connecter assembly 1000 illustrated in FIG. 3A is illustrated in FIG. 3B.

Next, referring to FIGS. 4A to 5C, an operation of dividing the connected connecter assembly 1000 into the male connecter 1 and the female connecter 2 will be described.

Figure 4A:
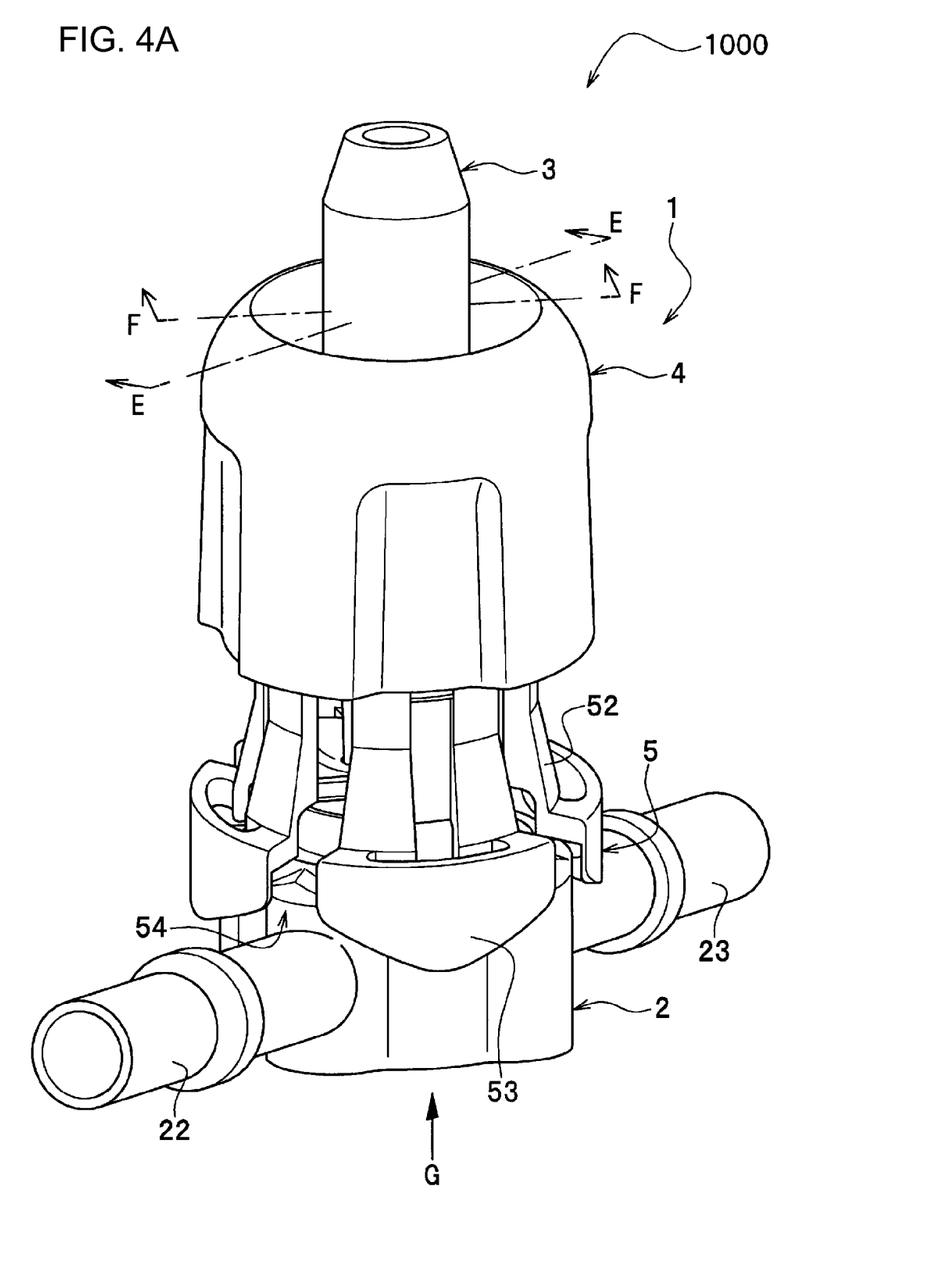
FIG. 4A is a perspective view of the connecter assembly when a lock member of the male connecter is moved upward.
Figure 4B:
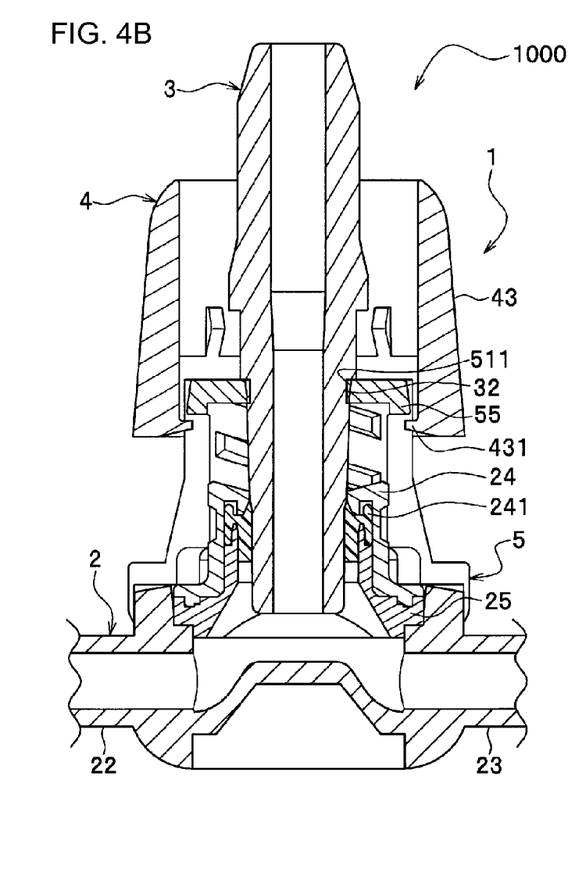
FIG. 4B is a cross-sectional diagram of the connecter assembly when the lock member of the male connecter is moved upward in the connecter assembly, taken along the line E-E of FIG. 4A.
Figure 4C:
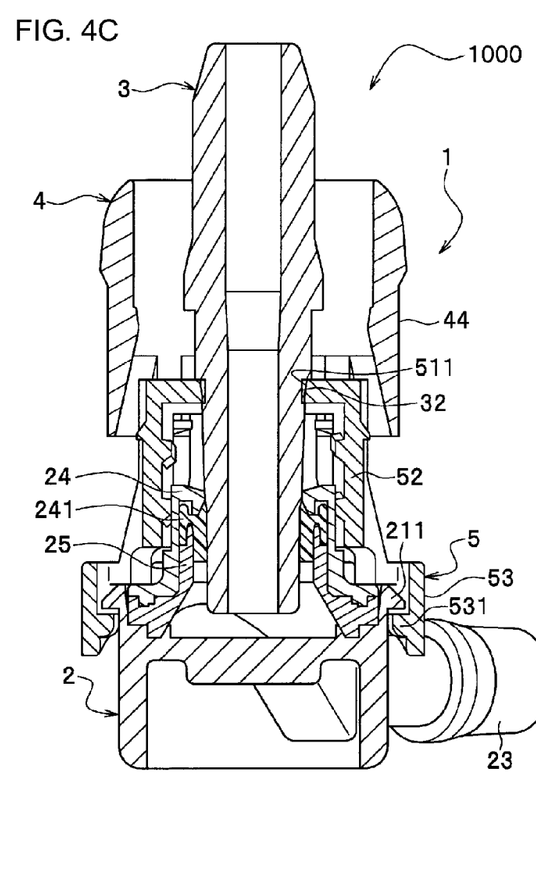
FIG. 4C is a cross-sectional diagram of the connecter assembly when the lock member of the male connecter is moved upward in the connecter assembly, taken along the line F-F of FIG. 4A.
Figure 4D:
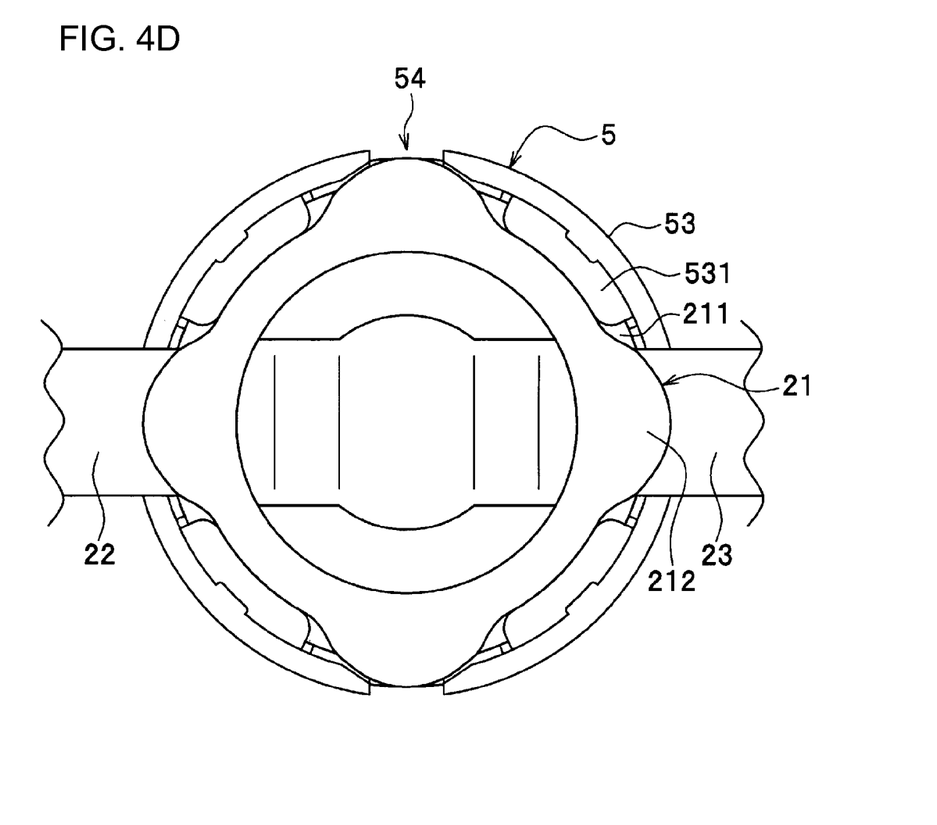
FIG. 4D is a bottom view of the connecter assembly (in a direction G shown in FIG. 4A) when the lock member of the male connecter is moved upward in the connecter assembly.

First, as illustrated in FIG. 4A, a user moves the lock member 4 upward and makes it away from the engagement member 5. Accordingly, the plurality of claw portions 53 of the engagement member 5, because restriction of movement with respect to the radially outward direction by the lock member 4 is released, is made to open in the radially outward direction (refer to FIGS. 4B and 4C). However, in this state, as illustrated in FIG. 4C, the claw 531 of the claw portion 53 of the engagement member 5 is engaged with the flange portion 211 of the main body portion 21 of the female connecter 2, so that the engagement member 5 is not disconnected from the female connecter 2.

Figure 2B:
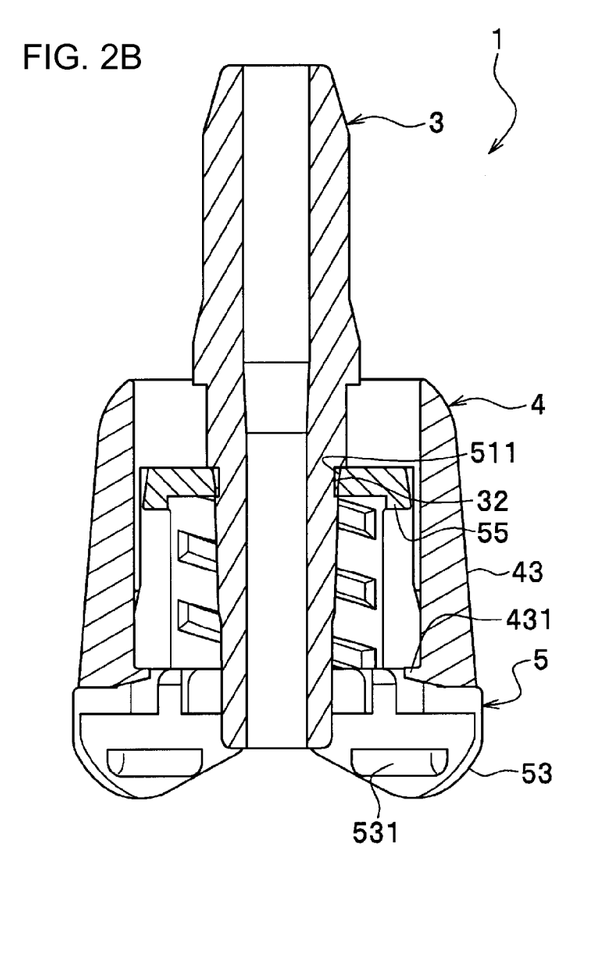
FIG. 2B is a cross-sectional diagram of the male connecter taken along the line A-A of FIG. 2A.

The lock member 4 and the engagement member 5 are only slightly fixed by bringing the convex portion 45 and the rib 56 into contact with each other (refer to FIG. 2B). Use thereof may make the lock member 4 and the engagement member 5 away from each other using a small force. In addition, when the lock member 4 and the engagement member 5 are away from each other, by bringing the rib 431 and the stopper 55 in contact with each other (refer to FIG. 4B), as long as the user does not apply a substantially large force, the lock member 4 is not completely disconnected from the engagement member 5.

Figure 5A:
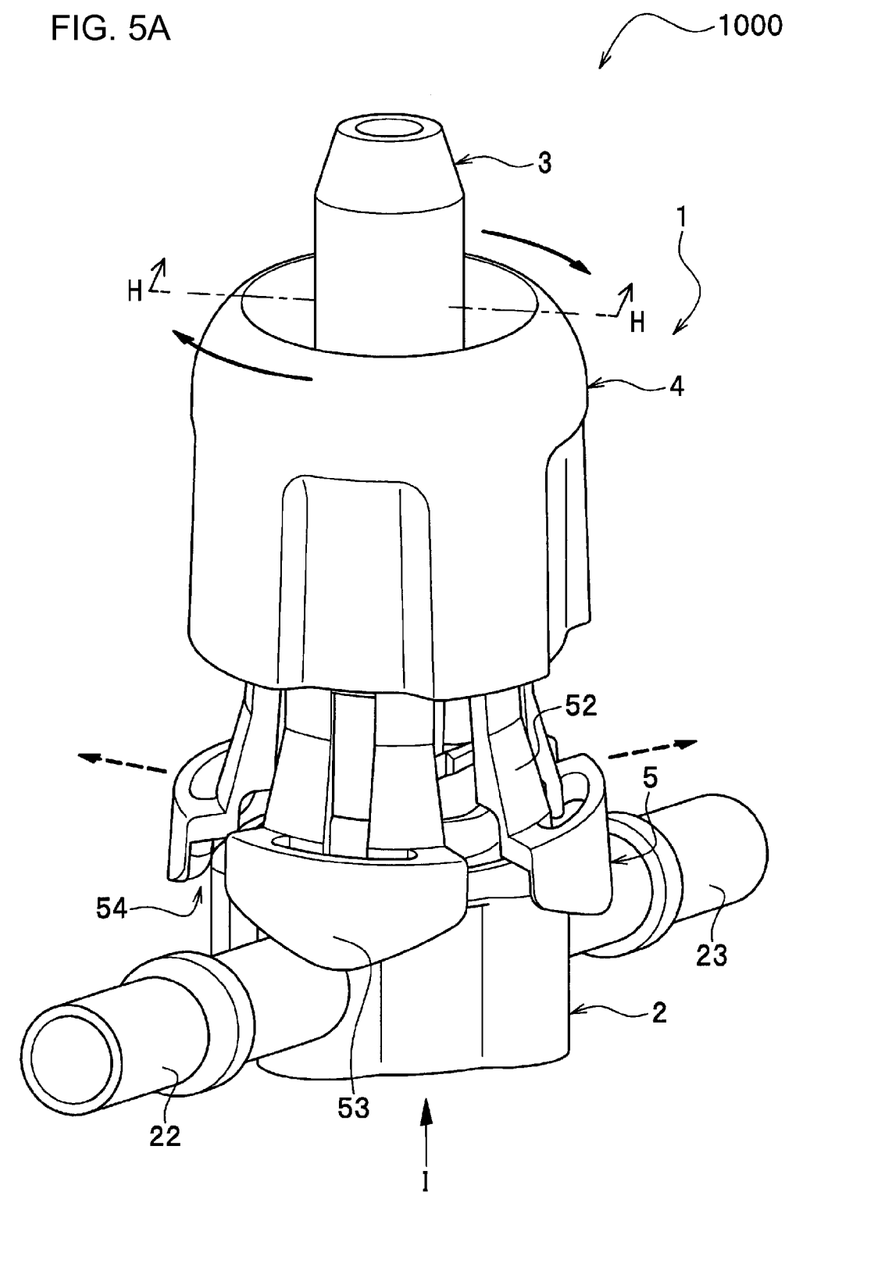
FIG. 5A is a perspective view of the connecter assembly when the lock member of the male connecter is moved upward and rotated in the connecter assembly.
Figure 5B:
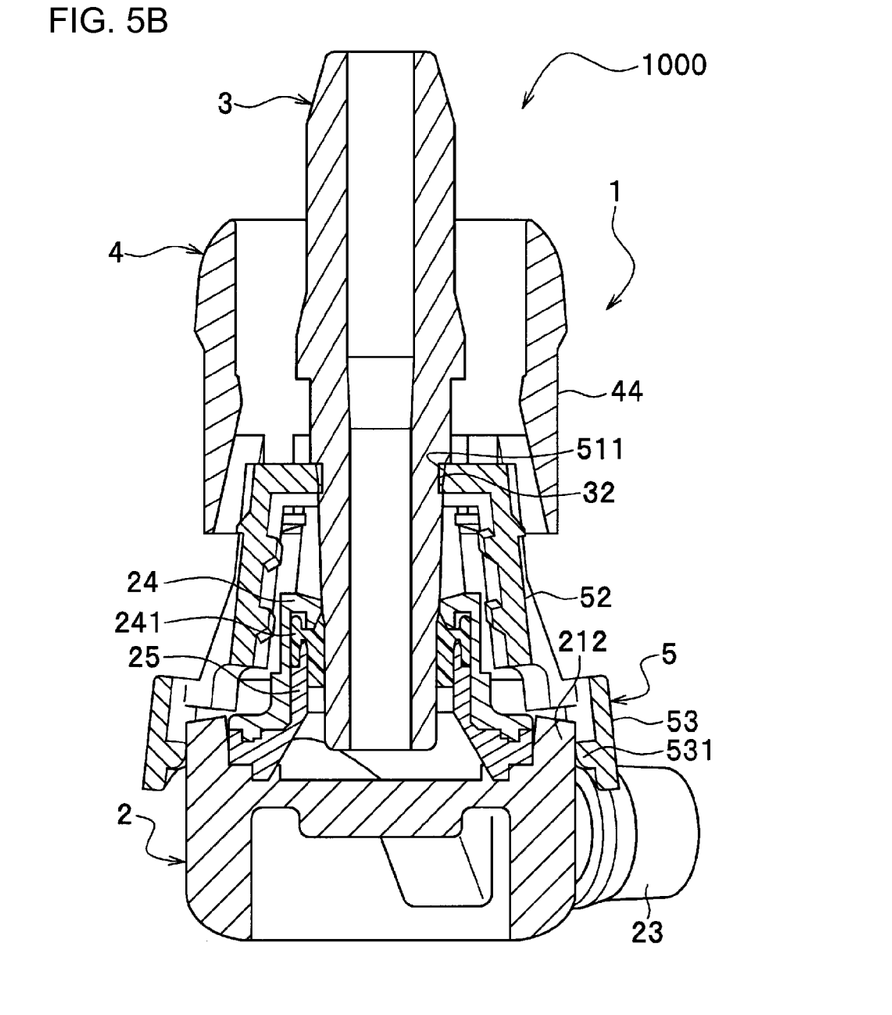
FIG. 5B is a cross-sectional diagram of the connecter assembly when the lock member of the male connecter is moved upward and rotated in the connecter assembly, taken along the line H-H in FIG. 5A.
Figure 5C:
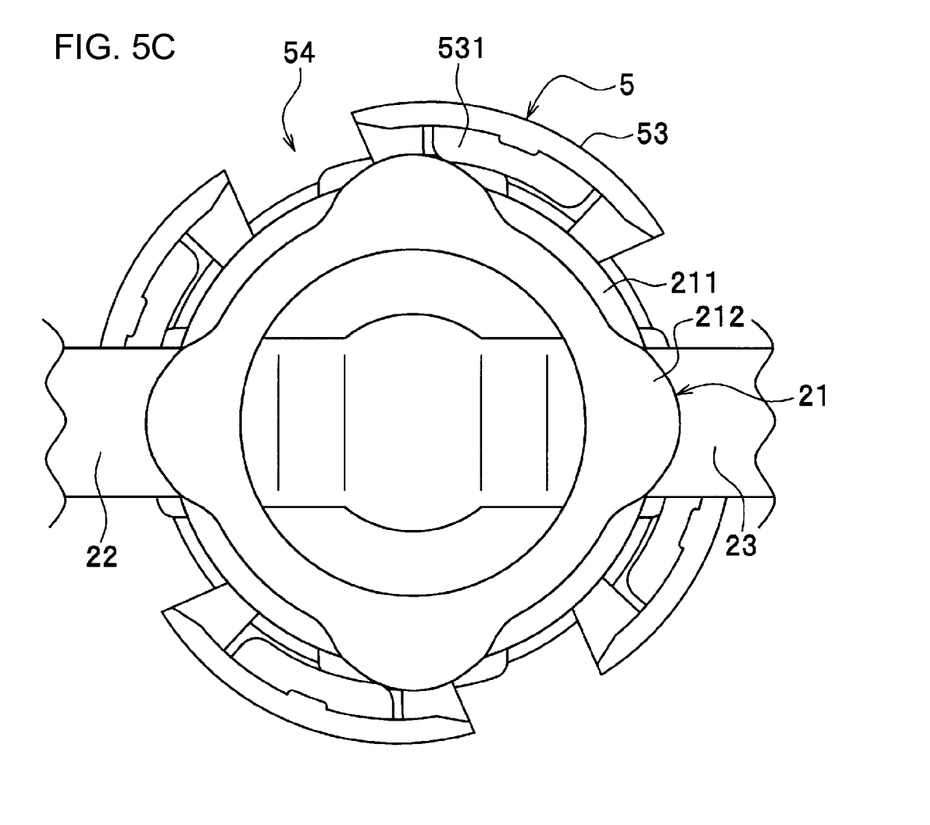
FIG. 5C is a bottom view of the connecter assembly (in a direction I shown in FIG. 5A) when the lock member of the male connecter is moved upward and rotated in the connecter assembly.

Next, a user, as illustrated in FIG. 5A, rotates the lock member 4, which is away from the engagement member 5, about 30 degrees clockwise. Then, the rib 431 of the lock member 4 is inserted to the slit portion 54 of the engagement member 5, so that, according to rotation of the lock member 4, the engagement member 5 is rotated.

Accordingly, the claw 531 of the plurality of claw portions 53 of the engagement member 5 rides on the plurality of non-flange portions 212 of the main body portion 21 (refer to FIGS. 5B and 5C), and is released from a state of being engaged with the flange portion 211. Thus, the male connecter 1 may be disconnected from the female connecter 2, and the user may separate the male connecter 1 and the female connecter 2 from each other when moving the male connecter 1 and the female connecter 2 in opposite directions to be positioned away from each other.

Therefore, according to the connecter assembly 1000 of the embodiment, it is possible to perform a connection operation between the male connecter 1 and the female connecter 2 as a first operation and to perform a disconnection operation of these as a second operation.

That is, in the connection operation of male connecter 1 and the female connecter 2, by pressing into each other, while connecting the connecter main body 3 of the male connecter 1 to the valve body 241 of the female connecter 2, each of (the claw 531 of) the claw portions 53 of the engagement member 5 of the male connecter 1 are engaged with each of the plurality of flange portions 211 of the main body portion 21 of the female connecter. Accordingly, it is possible to stably fix the male connecter 1 and the female connecter 2. In addition, by this fixation, it is possible to avoid a situation that the fixation is gradually loosened like a normal screw or the fixation is tightened too much to be loosened so as to prevent looseness.

In addition, in the disconnection of the male connecter 1 and the female connecter 2, firstly by a first operation of pulling away the lock member 4 of the male connecter 1 from the engagement member 5, and a second operation of rotating the lock member 4, the claws 531 of the plurality of claw portions 53 of the engagement member 5 of the male connecter 1 are eventually moved to each of the plurality of non-flange portions 212 from each of the plurality of flange portions 211 of the main body portion 21 of the female connecter 2 to enable disconnection between the male connecter 1 and the female connecter 2.

Therefore, it is possible to facilitate connection between the connecters and to reduce possibility of disconnection between the connecters in unintended situations. That is, in a state illustrated in FIG. 3A, even if attempting to rotate the lock member 4, the claw support portion 52 connected to the plurality of claw portions 53 of the engagement member 5 receives restriction of movement with respect to the radially outward direction by the lock member 4, so that the claw portion 53 may not be made to open to the radially outward direction. Then, since the non-flange portion 212 of the main body portion 21 of the female connecter 2 is bulged in a radially outward direction, the engagement member 5 may not be rotated. Accordingly, the lock member 4 which is engaged with the engagement member 5 in a rotation direction by the slit portion 54 and the rib 431 may not be rotated, either.

Each of the plurality of claw portions 53 of the engagement member 5 of the male connecter 1 and each of the plurality of non-flange portions 212 of the female connecter 2 are in a mountain shape. Accordingly, when performing a connection operation between the male connecter 1 and the female connecter 2, even without the positioning of the circumferential direction, each of the plurality of claw portions 53 of the engagement member 5 of the male connecter 1 is induced to a position of the flange portion 211 from the plurality of non-flange portions 212 of the female connecter 2, so that the connection operation is more facilitated.

In addition, the claw 531 of the claw portion 53 of the engagement member 5 of the male connecter 1, and a flange portion 211 of the female connecter 2 are plural in number. Accordingly, compared to a case where these are single in number, when the male connecter 1 and the female connecter 2 are connected to each other, it is possible to reduce a possibility and an extent of deformation (bending) of the member so that connection portions may get close to each other and the other portions may be away from each other.

Figure 2C:
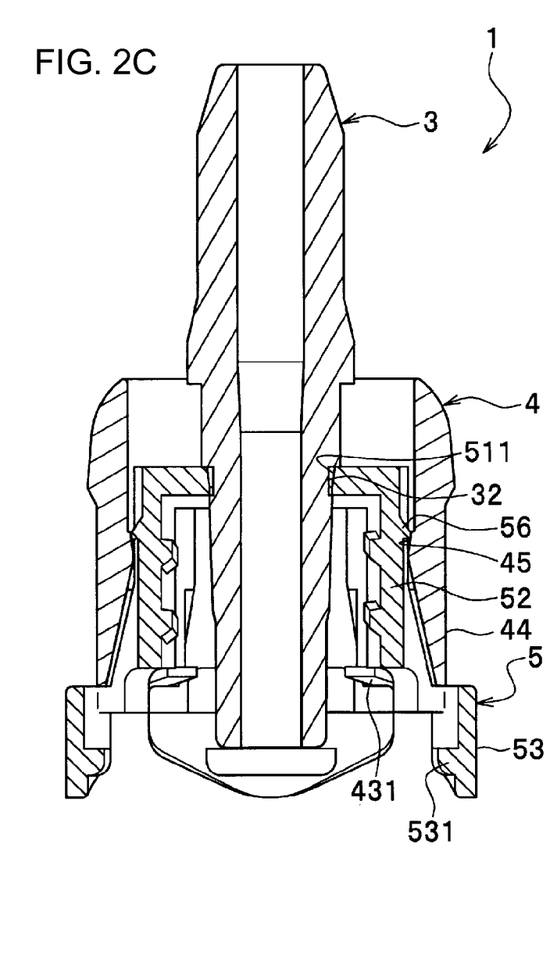
FIG. 2C is a cross-sectional diagram of the male connecter taken along the line a B-B of FIG. 2A.

As illustrated in FIGS. 2B and 2C, the male connecter 1 has a screw groove formed inside the claw support portion 52 of the engagement member 5. Accordingly, the male connecter 1 has the connecter main body 3 luer-fitted to the female connecter having a general shape of a screw thread which is known, and at the same time the engagement member 5 may be screw fitted.

In addition, as illustrated in FIG. 1, the female connecter 2 has a screw thread on the outer surface of the valve body support portion 24. Accordingly, with respect to the female connecter 2, a male connecter having a screw groove in a general shape which is known may be inserted to the valve body 241, and may be screw fitted to the valve body support portion 24 at the same time.

While certain embodiments of the present invention are described above, the present invention is not limited thereto.

For example, the number of the claw portions 53 and the slit portions 54 in the engagement member 5 is set to "4", but this may be other numbers like "6".

Further, a specific configuration of each unit and each means may be appropriately modified in without departing from the spirit of the present invention.

What is claimed is:

1. A connecter assembly comprising:
a male connecter and a female connecter that are connectable to each other,
wherein the male connecter includes:
a connecter main body;
an engagement member comprising:
a hole portion defining a hole in which the connecter main body is fixedly supported such that a surface of the connecter main body is engaged with a surface of the hole portion, and
a plurality of claw portions configured to engage with the female connecter; and
a lock member disposed outside the engagement member and configured to engage with the engagement member such that, when the lock member rotates in a circumferential direction of the male connecter, the engagement member rotates in the circumferential direction along with the lock member,
wherein the female connecter includes a main body portion, the main body portion including:
a plurality of flange portions protruding in a radially outward direction so as to be engagable with each of the plurality of claw portions of the engagement member of the male connecter, and
a plurality of non-flange portions that are disposed between the plurality of flange portions in a circumferential direction of the female connecter, and
wherein the male connecter and the female connecter are configured such that, when the male connecter is connected to the female connecter, the connecter main body of the male connecter is connected to the female connecter, and the plurality of claw portions of the engagement member of the male connecter engage with respective ones of the plurality of flange portions of the main body portion of the female connecter, thereby fixing the male connecter to the female connecter.

2. The connecter assembly according to claim 1, wherein a whole of the engagement member is in a substantially cylindrical shape.

3. The connecter assembly according to claim 1, wherein a whole of the lock member is in a substantially cylindrical shape.

4. The connecter assembly according to claim 1, wherein a whole of the main body portion is in a substantially cylindrical shape.

5. The connecter assembly according to claim 1, wherein, the male connecter is configured such that the lock member of the male connecter is movable in a direction away from the plurality of claw portions of the engagement member.

6. The connecter assembly according to claim 5, wherein, when the lock member is moved in the direction away from the plurality of claw portions of the engagement member, the plurality of claw portions of the engagement member are moveable in a radially outward direction.

7. The connecter assembly according to claim 6, wherein, when the lock member is moved in the direction away from the plurality of claw portions of the engagement member, the engagement member is rotatable in the circumferential direction of the male connecter.

8. The connecter assembly according to claim 7, wherein, when the lock member is rotated in the circumferential direction of the male connecter, each of the plurality of claw portions of the engagement member of the male connecter are moved to each of the plurality of non-flange portions from each of the plurality of flange portions of the main body portion of the female connecter.

9. The connecter assembly according to claim 1, wherein each of the plurality of claw portions of the engagement member of the male connecter and each of the plurality of non-flange portions of the female connecter include portions in a mountain shape which oppose each other when the male connecter and the female connecter are connected to each other.

10. The connecter assembly according to claim 1, wherein:
the engagement member of the male connecter further includes a plurality of slit portions provided between the plurality of claw portions, and
the lock member of the male connecter further includes a plurality of ribs that are slidably insertable into each of the plurality of slit portions of the engagement member.

11. The connecter assembly according to claim 1, wherein the non-flange portions of the female connecter are bulged in a radially outward direction relative to the flange portions.

12. A male connecter that is connectable to a female connecter that includes a main body portion, a plurality of flange portions protruding in a radially outward direction, and a plurality of non-flange portions that are disposed between the plurality of flange portions in a circumferential direction of the female connecter, the male connecter comprising:
a connecter main body;
an engagement member comprising:
a hole portion defining a hole in which the connecter main body is fixedly supported such that a surface of the connecter main body is engaged with a surface of the hole portion,
a plurality of claw portions configured to engage with the female connecter, and
a plurality of slit portions located between the plurality of claw portions in a circumferential direction of the engagement member; and
a lock member disposed outside the engagement member, the lock member including a plurality of ribs that are slidably insertable into the plurality of slit portions of the engagement member,
wherein the male connecter is configured such that:
when the male connecter is connected to the female connecter, the connecter main body of the male connecter is connected to the female connecter, and the plurality of claw portions of the engagement member of the male connecter engage with respective ones of the plurality of flange portions of the main body portion of the female connecter, thereby fixing the male connecter to the female connecter, and
when the male connecter is connected to the female connecter, the male connecter is disconnectable from the female connecter by moving the lock member in a direction away from the plurality of claw portions such that the plurality of ribs of the lock member are inserted into the plurality of slit portions of the engagement member, and rotating the lock member in a circumferential direction of the male connecter such that the engagement member rotates in the circumferential direction along with the lock member.

13. The male connecter according to claim 12, wherein a whole of the engagement member is in a substantially cylindrical shape.

14. The male connecter according to claim 12, wherein a whole of the lock member is in a substantially cylindrical shape.

15. The male connecter according to claim 12, wherein, when the lock member is moved in the direction away from the plurality of claw portions of the engagement member, the plurality of claw portions of the engagement member are moveable in a radially outward direction.

16. The male connecter according to claim 12, wherein the male connecter is configured such that when the lock member is rotated in the circumferential direction of the male connecter, each of the plurality of claw portions of the engagement member of the male connecter are moved.

17. The male connecter according to claim 10, wherein each of the plurality of claw portions of the engagement member of the male connecter includes portions in a mountain shape.

18. A method for using a connecter assembly that includes a male connecter and a female connecter, the method comprising:
   providing a male connecter that includes:
      a connecter main body;
      an engagement member including:
         a hole portion defining a hole in which the connecter main body is fixedly supported such that a surface of the connecter main body is engaged with a surface of the hole portion, and
         a plurality of claw portions configured to engage with the female connecter; and
      a lock member disposed outside the engagement member and configured to engage with the engagement member such that, when the lock member rotates in a circumferential direction of the male connecter, the engagement member rotates in the circumferential direction along with the lock member,
   providing a female connecter that includes a main body portion, the main body portion including:
      a plurality of flange portions protruding in a radially outward direction so as to be engagable with each of the plurality of claw portions of the engagement member of the male connecter, and
      a plurality of non-flange portions that are disposed between the plurality of flange portions in a circumferential direction of the female connecter,
   moving the lock member of the male connecter away from the plurality of claw portions;
   while the lock member is away from the claw portion, rotating the lock member and the engagement member in the circumferential direction of the male connecter;
   moving each of the plurality of the claw portions of the male connecter to each of the plurality of non-flange portions from each of the plurality of flange portions of the main body of the female connecter; and
   moving the male connecter and the female connecter away from each other in opposite directions.

\* \* \* \* \*